United States Patent
Russmann et al.

(10) Patent No.: US 9,943,441 B2
(45) Date of Patent: *Apr. 17, 2018

(54) APPARATUS AND METHOD FOR GENERATING CUT SURFACES IN THE CORNEA OF AN EYE FOR CORRECTION OF AMETROPIA

(71) Applicant: Carl Zeiss Meditec AG, Jena (DE)

(72) Inventors: Christoph Russmann, Jena (DE); Juergen Kuehnert, Jena (DE); Wilfried Bissmann, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,165

(22) Filed: Jan. 31, 2017

(65) Prior Publication Data
US 2017/0135856 A1     May 18, 2017

Related U.S. Application Data

(63) Continuation of application No. 14/619,830, filed on Feb. 11, 2015, now Pat. No. 9,572,716, which is a (Continued)

(30) Foreign Application Priority Data

Apr. 26, 2007   (DE) .......................... 10 2007 019 813

(51) Int. Cl.
  *A61F 9/008* (2006.01)

(52) U.S. Cl.
  CPC .......... *A61F 9/008* (2013.01); *A61F 9/00827* (2013.01); *A61F 9/00838* (2013.01);
(Continued)

(58) Field of Classification Search
  CPC .......... A61B 18/18; A61B 18/04; A61N 1/30; A61F 2/14
(Continued)

(56) References Cited

U.S. PATENT DOCUMENTS

| 5,123,902 A | 6/1992 | Mueller et al. |
| 5,620,437 A | 4/1997 | Sumiya |

(Continued)

FOREIGN PATENT DOCUMENTS

| CA | 2 620 095 A1 | 4/2007 |
| DE | 690 33 274 T2 | 4/2000 |

(Continued)

OTHER PUBLICATIONS

Intralase Product Leaflet, Essential Technology for Biomechanical Stability, Interlase Corp., 6 pages (2006).
(Continued)

*Primary Examiner* — William Thomson
*Assistant Examiner* — Victor Shapiro
(74) *Attorney, Agent, or Firm* — Patterson Thuente Pedersen, P.A.

(57) ABSTRACT

A method for generating cut surfaces in the cornea of an eye in order to correct ametropia using an apparatus. The method includes providing the apparatus including a laser unit, which focuses pulsed laser radiation into the cornea and moves the focused radiation in the cornea to generate cut surfaces, and a control unit, which controls the laser unit for generating cut surfaces. The method includes forming at least two mutually spaced apart cut surfaces as opening cuts by application of the pulsed laser radiation from the laser unit, each opening cut extending from an anterior corneal surface into the cornea and forming a further cut surface as a relieving cut by application of the pulsed laser radiation from the laser unit, which relieving cut extends from the
(Continued)

anterior corneal surface into the cornea. The position and shape of the relieving cut is selected such that the relieving cut contributes to the correction of the ametropia of the eye.

17 Claims, 4 Drawing Sheets

Related U.S. Application Data continuation of application No. 12/109,917, filed on Apr. 25, 2008, now Pat. No. 8,956,344.

(60) Provisional application No. 60/914,177, filed on Apr. 26, 2007.

(52) U.S. Cl.
CPC .............. *A61F 2009/00872* (2013.01); *A61F 2009/00885* (2013.01)

(58) Field of Classification Search
USPC .......... 606/4–6, 10–12, 27; 604/21; 623/5.11
See application file for complete search history.

(56) References Cited

U.S. PATENT DOCUMENTS

| | | | |
|---|---|---|---|
| 5,800,424 | A | 9/1998 | Sumiya |
| 5,891,132 | A | 4/1999 | Hohla |
| 5,919,185 | A | 7/1999 | Peyman |
| 5,970,984 | A | 10/1999 | Wakil et al. |
| 5,993,438 | A | 11/1999 | Juhasz et al. |
| 6,110,166 | A | 8/2000 | Juhasz |
| 6,210,399 | B1 | 4/2001 | Parel et al. |
| 6,364,875 | B1 | 4/2002 | Stanley, III |
| 6,730,074 | B2 | 5/2004 | Bille et al. |
| 7,131,968 | B2 | 11/2006 | Bendett et al. |
| 7,351,241 | B2 | 4/2008 | Bendett et al. |
| 8,182,471 | B2 | 5/2012 | Yee |
| 2002/0193704 | A1 | 12/2002 | Goldstein et al. |
| 2003/0014042 | A1 | 1/2003 | Juhasz et al. |
| 2004/0243111 | A1 | 12/2004 | Bendett et al. |
| 2008/0051772 | A1 | 2/2008 | Suckewer et al. |
| 2008/0065052 | A1 | 3/2008 | Bischoff et al. |
| 2008/0319428 | A1 | 12/2008 | Wiechmann et al. |

FOREIGN PATENT DOCUMENTS

| | | |
|---|---|---|
| DE | 10 2005 014 760 A1 | 10/2006 |
| DE | 10 2005 049 281 A1 | 4/2007 |
| EP | 1 941 849 B1 | 7/2010 |
| WO | WO 2004/105661 A1 | 12/2004 |

OTHER PUBLICATIONS

Jaycock et al., "Interferometric techinique to measure biomechanical changes in the cornea induced by refractive surgery," J. Cataract Refract Surg., vol. 31, pp. 174-184 (2005).

Lubatschowski et al., "Application of ultrashort laser pulses for intrastromal refractive surgery," Graefe's Arch Clin Exp Ophthalmol., vol. 238, pp. 33-39 (2000).

Luce, "Determining in vivo biomechanical properties of the cornea with an ocular response analyzer," J. Cataract Refract Surg., vol. 31, pp. 156-162 (2005).

Pinsky, "Computational modeling of mechanical anisotropy in the cornea and sclera," J. Cataract Refract Surg., vol. 31, pp. 136-145 (2005).

Rakay-Traub et al., "First Clinical Results with the Femtosecond Neodynium-glass Laser in Refractive Surgery," Journal of Refractive Surgery, vol., 19(2), pp. 94-103 (2003).

Application and File History for U.S. Appl. No. 12/109,917, filed Apr. 25, 2008. Inventors: Russmann et al.

Application and File History for U.S. Appl. No. 14/619,830, filed Feb. 11, 2015. Inventors: Russmann et al.

APPARATUS AND METHOD FOR GENERATING CUT SURFACES IN THE CORNEA OF AN EYE FOR CORRECTION OF AMETROPIA

CROSS-REFERENCE TO RELATED APPLICATIONS

This application is a continuation of U.S. application Ser. No. 14/619,830, filed Feb. 11, 2015 and entitled "Apparatus and Method for Generating Cut Surfaces in the Cornea of an Eye for Correction of Ametropia", now U.S. Pat. No. 9,572,716, which in turn is a continuation of U.S. application Ser. No. 12/109,917, filed Apr. 25, 2008 and entitled "Apparatus and Method for Generating Cut surfaces in the Cornea of an Eye for Correction of Ametropia," now U.S. Pat. No. 8,956,344, which claims priority to German Application No. 10 2007 019 813.4, filed Apr. 26, 2007 and to U.S. Provisional Application No. 60/914,177, filed Apr. 26, 2007, the disclosures of all of which are hereby incorporated by reference.

BACKGROUND

1. Field of the Invention

The invention relates to an apparatus for generating cut surfaces in the cornea of an eye in order to correct ametropia, said apparatus comprising a laser unit, which can focus pulsed laser radiation for generating cut surfaces into the cornea and move the radiation therein, and a control unit, which controls the laser unit for generating cut surfaces such that a predetermined lenticle to be removed is separated from the surrounding corneal material in the cornea by at least one cut surface and such that at least two mutually spaced apart cut surfaces are formed as opening cuts, each extending from the lenticle to the anterior corneal surface.

The invention further relates to a method for generating cut surfaces in the cornea of an eye in order to correct ametropia, wherein the pulsed laser radiation for generating cut surfaces is focused into the cornea and moved therein such that a predetermined lenticle to be removed is separated from the surrounding corneal material in the cornea by at least one cut surface and such that at least two mutually spaced apart cut surfaces are formed as opening cuts, each extending from the lenticle to the anterior corneal surface.

2. Background

Such apparatus and method are known, for example, from WO 2004/105661 A1. However, the desired correction of ametropia of the eye is frequently not achieved by such apparatus and method.

SUMMARY

In view thereof, it is an object of the invention to improve an apparatus of the above-mentioned type to overcome the described disadvantage. Further, a corresponding method of the invention is improved accordingly.

Said object is achieved by an apparatus of the type mentioned above for generating cut surfaces in the cornea of an eye in order to correct ametropia in that the position and shape of the opening cuts are selected such that the opening cuts contribute to the correction of the ametropia of the eye or do not counteract the correction of the ametropia of the eye.

It has been discovered that the opening cuts themselves, although being very small, may lead to an undesirable deterioration of the eye's ametropia. Since this effect of the opening cuts is now being taken into account for the first time by the apparatus of the invention, this advantageously allows the opening cuts to contribute to the correction of ametropia or not to counteract the correction of the eye's ametropia. The opening cuts according to the invention accomplish the foregoing advantages because they are neutral with respect to the ametropia to be corrected and/or do not cause any additional ametropia. Thus, for example, when correcting myopia or hyperopia, the opening cuts can be prevented from causing an undesired astigmatism.

Thus, the apparatus according to the invention for generating cut surfaces in the cornea of an eye in order to correct ametropia advantageously benefits from the fact that an opening cut, which is to be provided and through which the lenticle can be removed, is also simultaneously taken into account with respect to the correction of the eye's ametropia. It has turned out that favorable results can be achieved by providing two or more opening cuts. Providing two or more opening cuts has the advantage that they can be used, for example, to rinse the area being operated on (cut area of the lenticle).

Further, the inclusion of the opening cuts in the correction of ametropia is advantageous insofar as the lenticle volume to be removed can be minimized. Thus, reductions in thickness from several μm up to 100 μm can be achieved. This allows, for example, minimizing mechanical weakening of the cornea, if such weakening is caused by material removal or lenticle removal, respectively.

The opening cuts are provided such that it is not possible to fold back a corneal lamella as in the known LASIK operation (laser in situ keratomileusis). Thus, the opening cuts do not lead to a flap of the type provided and folded back in the LASIK operation.

The ametropia to be corrected may be, for example, myopia, hyperopia, astigmatism or presbyopia. It is also possible for the present invention to correct higher-order errors of refracting power. In particular, fourth-order errors of refracting power (spherical aberrations) lead to problems with night vision. Thus, these errors of refracting power of the cornea, or ametropias, can also be corrected by the apparatus according to the invention.

The present control unit may control the laser unit to thereby generate at least three mutually spaced apart opening cuts such that the centers of area of the opening cuts coincide with the corners of a regular polygon. In this case, it is possible, for example, that the opening cuts do not cause additional astigmatism.

The geometrical shape may be the same for each opening cut, although it is also possible to select different geometrical shapes. Thus, for example, the control unit may control the laser unit such that the cut length of at least one opening cut from the anterior corneal surface to the lenticle differs from the cut length of the other opening cuts.

Further, the control unit may control the laser unit to generate exactly two mutually spaced apart opening cuts such that the centers of area of the opening cuts are located on a straight line which, when viewed in a top view of the eye, is parallel to one axis of astigmatism of the eye or intersects said axis at a maximum angle of 10°. This enables a correction for astigmatism. Preferably, the steepest axis of astigmatism is selected (i. e., that axis in relation to which the greatest astigmatism is present).

The control unit can control the laser unit such that at least one of the opening cuts, when viewed in a top view of the eye, has the geometrical shape of a circular ring segment. This shape can be realized with particular ease using conventional laser units in ophthalmic correction apparatuses.

In particular, the control unit can control the laser unit such that the opposite straight sides of the circular ring segment enclose an angle of 30°-120°, 45°-80°, or 30°-60°.

Further, the control unit can control the laser unit such that the opposite straight sides of the circular ring segment have a length of 0.1-1 mm or 0.2-0.4 mm, when viewed in a top view.

In the apparatus according to the invention, the control unit can control the laser unit such that a further cut surface is provided as a relieving cut, which extends from the anterior corneal surface into the cornea, but not up to the lenticle. The location and shape of the relieving cut may be selected so as to contribute to the correction of the eye's ametropia. Of course, several relieving cuts can be provided. Due to the additional relieving cut or cuts, an effective correction of ametropia can be achieved.

The control unit can control the laser unit such that at least one of the cut surfaces is generated as a perforated cut surface. A perforated cut surface is understood herein to be a cut surface which is not entirely continuous, but comprises material bridges which break away under a predetermined mechanical load (for example, by removal of the lenticle).

In a method of the above-mentioned type, the location and shape of the opening cuts are selected such that they contribute to the correction of the eye's ametropia or do not counteract the correction of the eye's ametropia.

Using the method according to the invention, it is therefore possible to provide the required opening cuts such that they contribute to the correction of ametropia or do not counteract the correction of ametropia. This makes it possible to minimize the material volume of the lenticle to be removed. In particular, the lenticle need not be provided, for example, to compensate for imaging errors caused by the opening cuts, which would otherwise disadvantageously lead to a greater material volume to be removed from the cornea.

In the method of this invention, the position and shape of the opening cuts may be selected such that the correction of the ametropia of the eye is not counteracted in such a manner that the opening cuts do not generate additional astigmatism of the eye. This makes it possible to correct myopia or hyperopia in which the patient, while no longer being near-sighted or far-sighted, has an ametropia in the form of an astigmatism.

The ametropia to be corrected may be myopia, hyperopia, astigmatism and/or presbyopia. The ametropia may further comprise higher-order errors of refracting power, as well. In particular, the ametropia may include fourth-order errors of refracting power such as spherical aberration, which plays a major role in night vision capacity.

In the method of this invention, at least three mutually spaced apart opening cuts can be generated such that their centers of area coincide with the corners of a regular polygon. In this case, it is probable that the opening cuts will not cause additional astigmatism.

The cut length of at least one opening cut from the anterior corneal surface to the lenticle may be made to differ from the cut lengths of the other opening cuts. The opening cuts may also have the same or differing geometrical shapes and/or dimensions.

In one method of the invention, exactly two mutually spaced apart opening cuts can be generated such that their centers of area are located on a straight line which, when viewed in a top view of the eye, is parallel to an axis of astigmatism of the eye (preferably the steepest axis of astigmatism) or intersects said axis at a maximum angle of 10°. Such spaced apart opening cuts enable effective correction of astigmatism.

These opening cuts may be executed such that at least one of the opening cuts, when viewed in a top view of the eye, has the geometrical shape of a circular ring segment. Such a shape can be easily realized using a laser unit of a conventional ophthalmic correction apparatus.

In particular, the opening cut may be carried out such that the opposite straight sides of the circular ring segment enclose an angle of 30°-120°, 45°-80°, or 30°-60°.

Further, the at least one opening cut may be carried out such that opposite straight sides of the circular ring segment has a length of 0.1-1 mm or 0.2-0.4 mm.

In one present method, a further cut surface may be formed as a relieving cut, extending from the anterior corneal surface into the cornea, but not up to the lenticle. The position and shape of the relieving cut may be selected such that the cut contributes to the correction of the ametropia. One or several mutually spaced apart relieving cuts can be formed, the opening cut(s) enable(s) improving correction of ametropia.

In one present method, at least one of the cut surfaces may be formed as a perforated cut surface, thereby resulting in smoother cut surfaces, as compared to cut surfaces produced as continuous cut surfaces by pulsed laser radiation.

In particular, one method of this invention allows the lenticle separated from the surrounding corneal material to be removed from the cornea through one of the opening cuts.

It is further possible to divide the lenticle into two or more parts by the pulsed laser radiation and to remove said parts of the lenticle from the cornea through one or more opening cuts.

Further, the opening cuts may also be used to effect flushing of the cut surfaces or, where applicable, to introduce drugs.

Further, a method is provided for generating control data for a control unit of a correcting apparatus for generating cut surfaces in the cornea of an eye. The correcting apparatus may comprise a laser unit and a control unit. The laser unit may focus pulsed laser radiation into the cornea in order to generate cut surfaces and move said radiation therein. The control unit for the laser unit generates control data, thereby allowing the control unit to control the laser unit, on the basis of the control data to generate cut surfaces, such that a predetermined lenticle to be removed is separated from the surrounding corneal material in the cornea through at least one cut surface and such that at least two mutually spaced apart cut surfaces are provided as opening cuts. Each opening cut may extend from the lenticle to the anterior corneal surface. The position and shape of the opening cuts may be predetermined by the control data, such that the opening cuts contribute to correction of the ametropia of the eye or do not counteract the correction of the ametropia of the eye.

The present method for generating control data may be further embodied such that further embodiments of the inventive method for generating cut surfaces in the cornea of an eye in order to correct ametropia can be carried out.

The cut surfaces may be generated in the cornea using the apparatus according to the present invention and the present method by pulsed laser radiation. Several processes may take place in the tissue within a time sequence. These processes may be initiated by pulsed laser radiation. If the power density of the radiation is above a threshold value during any pulse, an optical breakthrough may appear which, for example, would form a plasma bubble in the cornea. The plasma bubble then grows, due to expanding gas after the optical breakthrough has formed. If the optical breakthrough is not maintained, the gas generated in the plasma bubble is absorbed by the surrounding tissue, and the bubble disappears. Tissue-separating effects, acting without plasma bubbles, are also possible. For the sake of simplicity, all such processes, including their effects, are summarized here by the term "optical breakthrough."

For tissue separation to occur, the laser radiation may be applied in pulsed form, with the pulse duration usually being below 1 ps. Thus, the power density required for the respective pulse to initiate the optical breakthrough is achieved within a narrow spatial area. High focusing of the laser beam in combination with the short pulses allows the optical breakthrough to be placed in the cornea with pinpoint accuracy. For cut surface generation, a series of optical breakthroughs is generated at the corresponding locations for the cut surface.

It will be appreciated that the features mentioned above and those yet to be explained below can be used not only in the indicated combinations, but also in other combinations or alone, without departing from the scope of the present invention.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
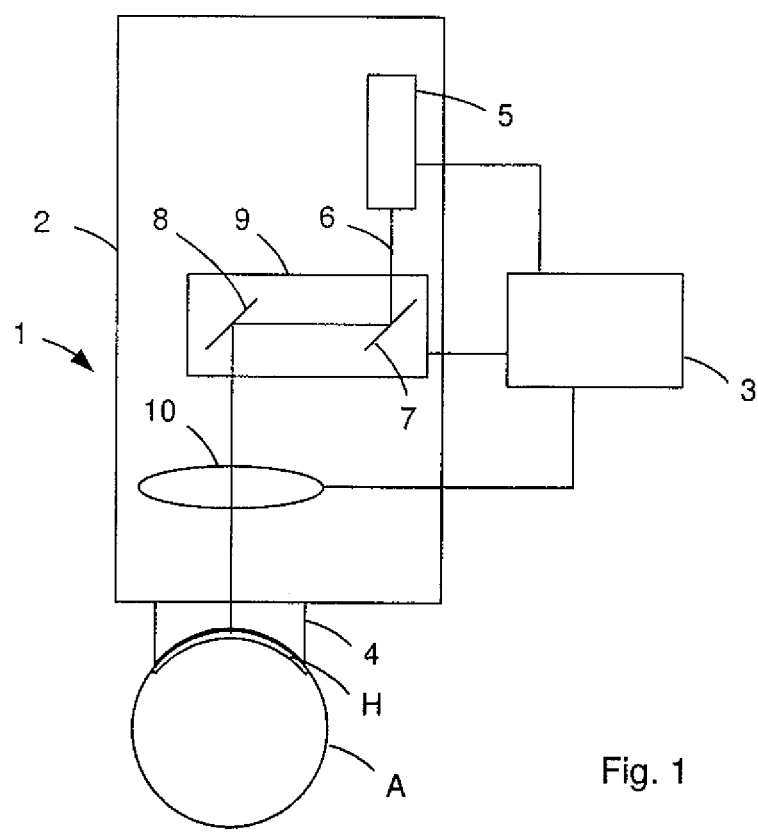
FIG. 1 shows a schematic view of an embodiment of the correcting device according to the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

In the embodiment shown in FIG. 1, the apparatus 1 for generating cut surfaces in the cornea H of an eye A in order to correct ametropia comprises a laser unit 2 and a control unit 3 for control of the laser unit 2. Further, the apparatus 1, which is also referred to hereinafter as a correcting apparatus, may comprise a contact element 4 which is detachably coupled with the laser unit 2 and with which the eye A to be corrected is in contact during operation of the apparatus 1.

As is evident from the schematic representation of FIG. 1, the laser unit 2 comprises a laser 5 emitting pulsed laser radiation 6. In this case, the pulse duration is, for example, in the femtosecond range (e.g. 50-800 fs) at a pulse repetition frequency of between 10 and 1 MHz.

The pulsed laser radiation 6 is focused through the contact element 4, by two deflecting mirrors 7, 8 forming a scanner 9 and by optics 10, into the cornea H of an eye A contacting the contact element 4 and is moved in the cornea H. This is effected under the control of the control unit 3, so that basically any locations in the cornea can have the pulsed laser radiation 6 applied thereon.

Of course, the scanner may also be designed in any other manner known to the person skilled in the art.

The control unit 3 may control the laser unit 2 such that an optical breakthrough for tissue separation is generated at the respective focus location in the cornea H. The focus locations are selected to be adjacent each other such that a desired cut surface can be generated in the cornea H. The focus locations may be adjacent each other such that the tissue is cut through completely between the focus locations. However, it is also possible that small tissue bridges remain, so that the cut surface can be referred to as a perforated cut surface.

The laser unit 2 and the control unit 3 are shown in a schematic and simplified manner in FIG. 1. Thus, for example, the optics 10, depicted as a lens, may comprise several optical elements, suitably arranged along the beam path from the laser 5 to the contact element 4.

The correction apparatus 1 may be operated such that, in order to correct ametropia (in this case, for example, correction of myopia and astigmatism), a preferably lens-shaped partial volume 11 (hereinafter also referred to as a lenticle) in the cornea H is separated from the surrounding corneal material by the pulsed laser radiation 6. This is preferably carried out such that first the rear surface 12 (FIG. 3) of the lenticle 11 and then the front surface 13 of the lenticle 11 is cut. In order to allow the lenticle 11, separated from the residual corneal material, to be removed from the cornea H, first and second opening cuts 14, 15, each extending from the lenticle 11 to the anterior corneal surface 16, are provided, as schematically shown in FIGS. 2 and 3.

The lenticle 11 can then be removed from the cornea H in a known manner through the first or second opening cut 14, 15. Due to the missing corneal volume (lenticle 11), the cornea will change its shape in this area. Prior to carrying out the method, the shape of the lenticle was selected such that the shape of the cornea after removal of the lenticle results in the desired correction of ametropia.

Figure 2:
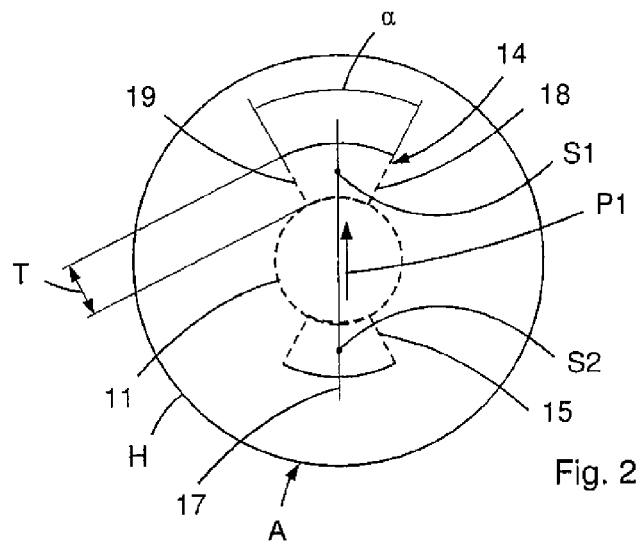
FIG. 2 shows a top view of an eye after carrying out the method according to the invention for generating cut surfaces in the cornea of an eye for correction of ametropia.
Figure 3:
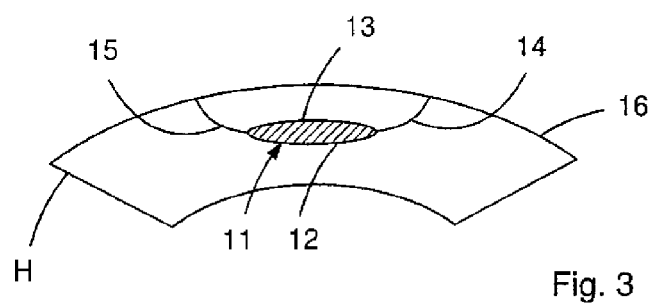
FIG. 3 shows a cross-sectional view of the cornea H along the line 17 of FIG. 2.

In the described exemplary embodiment of FIGS. 2 and 3, two opening cuts 14 and 15 have been performed and the shapes and positions of the opening cuts 14 and 15 are selected such that any still existing astigmatism of the eye A is also corrected thereby.

In other words, the invention takes into consideration the fact that even the very small opening cuts 14 and 15 may have an influence on the astigmatism of the eye A. This per se undesired effect is used in the invention to correct an existing astigmatism of the eye A.

In the described exemplary embodiment, it is assumed that the steepest axis of astigmatism in FIG. 2 extends from top to bottom as indicated by the arrow P1. In this case, the two opening cuts 14 and 15 are arranged such that their centers of area S1 and S2 are located on a straight line 17, which is parallel to or coincides with, the axis of astigmatism P1. Merely for the sake of clearer illustration, FIG. 2 shows the axis of astigmatism P1 slightly laterally of the straight line 17.

By this arrangement of the opening cuts 14 and 15, the astigmatism of the eye A is reduced due to the opening cuts 14 and 15.

As is evident from FIG. 2, the opening cuts 14 and 15, when viewed in the top view of FIG. 2, are respectively provided as circular ring segments. Since both opening cuts 14 and 15 are identical, only the first opening cut 14 will be described in more detail below.

The two straight sides 18 and 19 of the opening cut 14 have the same length T (FIG. 2), said length being between 0.1 and 1 mm or between 0.2 and 0.4 mm in the exemplary embodiment described here. Further, the two straight sides 18 and 19 enclose an angle α, which may range from 30°-120° or from 40°-80°.

Figure 4:
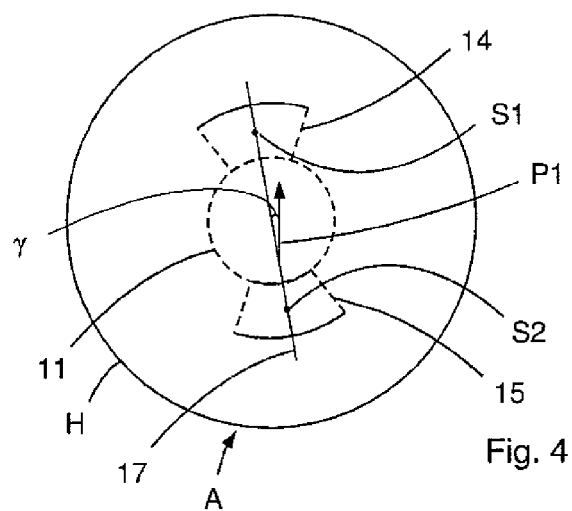
FIG. 4 shows a top view of an eye after carrying out the correcting method of the invention according to another embodiment.

FIG. 4 shows a modification of the embodiment of FIGS. 2 and 3. In this modification, the opening cuts 14 and 15 are placed such that the straight line 17 connecting the centers of area S1, S2 encloses an angle γ with the axis of astigmatism P1, said angle being 10° here. Even with this modification, an excellent correction of astigmatism is still achieved by the opening cuts 14 and 15.

Figure 5:
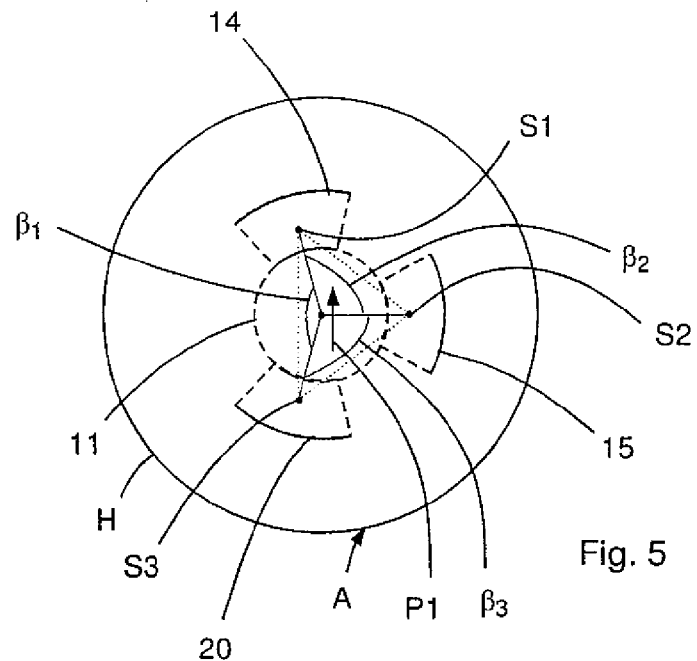
FIG. 5 shows a top view of an eye after carrying out the correcting method of the invention according to yet another embodiment.

As is evident from the embodiment shown in FIG. 5, three opening cuts 14, 15 and 20 have been carried out. The opening cuts 14, 15 and 20 are mutually spaced apart, with the centers of area S1, S2 and S3 defining a triangle, which is indicated by a dotted line in FIG. 5.

In order to achieve a correction of astigmatism by the opening cuts 14, 15 and 20, the opening cuts 14, 15 and 20 are located at unequal angular distances from one another on the circumference of the lenticle 11, as is evident from FIG. 5. Thus, the angle $\beta_1$ is 150° and the angles $\beta_2$ and $\beta_3$ are each 105°. Due to this asymmetrical angular distribution of the opening cuts 14, 15 and 20, the desired correction of astigmatism is achieved.

Figure 6:
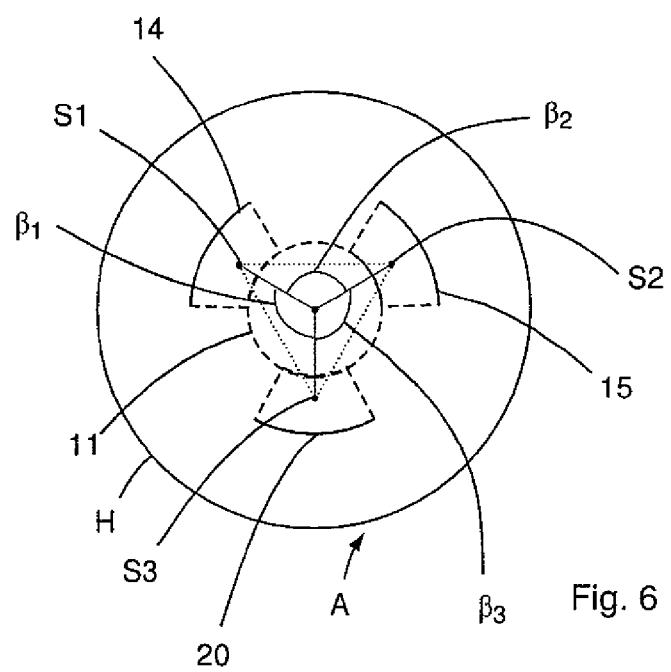
FIG. 6 shows a top view of an eye after carrying out the correcting method of the invention according to another embodiment.

However, it is also possible to distribute the opening cuts 14, 15 and 20 at equal angles, as shown in FIG. 6. In this case, the angles $\beta_1$, $\beta_2$ and $\beta_3$ are each 120°. This distribution of the opening cuts is selected if no correction of astigmatism by the opening cuts 14, 15 and 20 is desired. This may be the case, for example, if no astigmatism, but only a myopia has to be corrected. Thus, the opening cuts 14, 15 and 20 can be provided such that there is no influence on the astigmatism. As is evident from FIG. 6, the triangle defined by the centers of area S1, S2 and S3 is then an equilateral triangle.

Further, it is possible for the opening cuts 14, 15 and 20 in FIG. 6 to be arranged and shaped such that they contribute to the desired correction of myopia.

Figure 7:
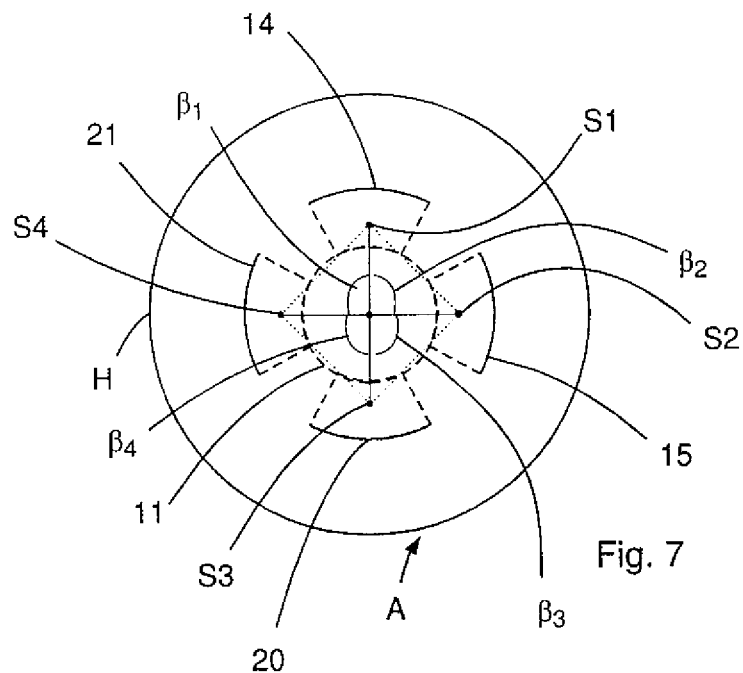
FIG. 7 shows a top view of an eye after carrying out the correcting method of the invention according to yet another embodiment.

Providing the opening cuts without influencing the astigmatism of the cornea H is also possible in the case of four opening cuts, as shown in FIG. 7. The four opening cuts 14, 15, 20 and 21 are again distributed at equal angles on the circumference of the lenticle 11 so that, in this case, the centers of area S1, S2, S3 and S4 define a square.

In general, it can be said that n opening cuts (with n>2) can be provided such that their centers of area form a regular n-sided polygon so as to cause no influence on astigmatism by the n opening cuts.

Figure 8:
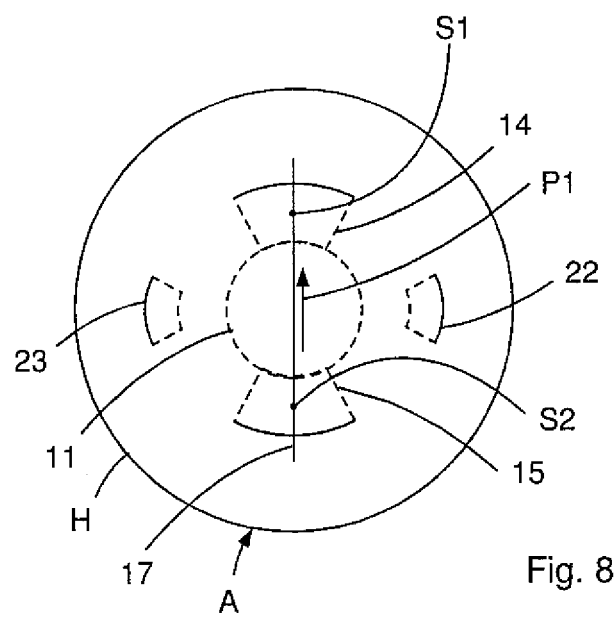
FIG. 8 shows a top view of an eye after carrying out the correcting method of the invention according to another embodiment.

As indicated in FIG. 8, which shows a further development of the embodiments of FIGS. 2 and 3, relieving cuts 22, 23 can be carried out in addition to the opening cuts 14, 15, said relieving cuts extending from the anterior surface of the cornea H into the latter, but not up to the lenticle 11. These relieving cuts 22, 23 can be used in order to correct the ametropia to be corrected by the lenticle 11 and/or of the astigmatism (arrow P1).

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. §112(f) are not to be invoked unless the specific terms "means for" or "step for" are recited in a claim.

The invention claimed is:

1. A method for generating cut surfaces in a cornea of an eye to correct ametropia using an apparatus, said method comprising:
providing the apparatus including a laser unit, which focuses pulsed laser radiation into the cornea at a focal point and moves said focal point within the cornea to generate cut surfaces within the cornea, and a control unit, which controls the laser unit for generating cut surfaces;

forming at least one cut surface as an opening cut by application of the pulsed laser radiation from the laser unit, the opening cut extending from an anterior corneal surface into the cornea;

forming at least one further cut surface as a relieving cut by application of the focused pulsed laser radiation from the laser unit, the relieving cut extending from the anterior corneal surface into the cornea and not extending to a cut surface of a lenticle formed in the cornea; and selecting a position and a shape of the relieving cut such that the relieving cut contributes to the correction of the ametropia of the eye.

2. The method as claimed in claim 1, further comprising forming several relieving cuts and selecting a position and a shape of each relieving cut such that the relieving cuts contribute to the correction of the ametropia of the eye.

3. The method as claimed in claim 1, further comprising selecting a position and a shape of each opening cut such that the opening cuts do not counteract the correction of the ametropia of the eye.

4. The method as claimed in claim 1, further comprising generating at least one of the cut surfaces as a perforated cut surface.

5. The method as claimed in claim 1, further comprising selecting a position and a shape of each opening cut such that the opening cuts do not generate any additional astigmatism of the eye.

6. The method as claimed in claim 1, wherein the ametropia to be corrected comprises an astigmatism of the eye.

7. The method as claimed in claim 1, further comprising using at least one of the opening cuts to rinse an area being operated.

8. The method as claimed in claim 1, wherein the pulsed laser radiation is generated with a pulse duration below 1 ps.

9. The method as claimed in claim 1, further comprising forming at least two mutually spaced apart cut surfaces as the opening cuts by application of the pulsed laser radiation from the laser unit, each opening cut extending from the anterior corneal surface into the cornea.

10. A method for generating cut surfaces in the cornea of an eye to correct ametropia using an apparatus, said method comprising:

providing the apparatus including a laser unit, which focuses pulsed laser radiation into the cornea and moves said focused pulsed radiation in the cornea to generate cut surfaces within the cornea, and a control unit;

controlling the laser unit with the control unit to form at least one cut surface as at least one opening cut by application of the pulsed laser radiation from the laser unit, the at least one opening cut extending from an anterior corneal surface into the cornea and extending to a cut surface of a lenticle formed in the cornea, the at least one opening cut being formed as a circular ring segment or wherein the at least one opening cut includes at least two opening cuts that are mutually spaced apart and are arranged symmetrically or asymmetrically around the lenticle; and selecting a position and a shape of the at least one opening cut such that the at least one opening cut contributes to the correction of the ametropia of the eye.

11. The method as claimed in claim 10, further comprising:

forming a further cut surface as a relieving cut, the relieving cut extending from the anterior corneal surface into the cornea; and selecting a position and a shape of the relieving cut such that the relieving cut contributes to the correction of the ametropia of the eye.

12. The method as claimed in claim 11, wherein several relieving cuts are formed and a position and a shape of each relieving cut is selected such the relieving cuts contribute to the correction of the ametropia of the eye.

13. The method as claimed in claim 10, further comprising generating at least one of the cut surfaces as a perforated cut surface.

14. The method as claimed in claim 10, further comprising selecting a position and a shape of the at least one opening cut such that the at least one opening cuts does not generate any additional astigmatism of the eye.

15. The method as claimed in claim 10, wherein the ametropia to be corrected comprises an astigmatism of the eye.

16. The method as claimed in claim 10, further comprising using the at least one opening cuts to rinse an area being operated.

17. The method as claimed in claim 10, further comprising generating the pulsed laser radiation with a pulse duration below 1 ps.

* * * * *